United States Defensive Publication [19] (H) [11] T103,803

Lok et al. [43] Jan. 3, 1984

[54] PHOTOGRAPHIC SPEED INCREASING AND LATENT IMAGE STABILIZING COMPOUNDS, SILVER HALIDE EMULSIONS, AND PHOTOGRAPHIC ELEMENTS

[76] Inventors: Roger Lok, Hilton; John P. Freeman, Rochester; William N. Baum, Henrietta, all of N.Y.

[21] Appl. No.: 408,536

[22] Filed: Aug. 16, 1982

Related U.S. Application Data

[62] Division of Ser. No. 320,794, Nov. 11, 1981, Pat. No. 4,378,426.

[51] Int. Cl.[3] ..... C07D 277/82; C07D 263/58; C07D 235/30

[52] U.S. Cl. ..... 548/121; 430/505; 430/551; 430/600; 430/614; 548/161; 548/179; 548/217; 548/222; 548/329; 548/330

[57] ABSTRACT

Photographic silver halide emulsions show increased speed and reduced latent image fading when a compound of the following structure is incorporated:

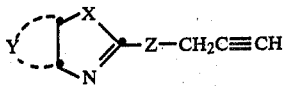

wherein:

X is —O—, —S—, —Se—, or $$-\overset{R}{N}-;$$

Y represents the atoms completing a fused aromatic nucleus;

Z is $$-CH_2\overset{R}{N}- \quad \text{or} \quad -\overset{R}{N}-;$$

and

R is hydrogen or lower alkyl of from 1 to 5 carbon atoms.

2 Claims, No Sheets Drawing,

22 Pages Specification

The file of this unexamined application may be inspected and copies thereof may be purchased (849 O.G. 1221, Apr. 9, 1968).